(12) United States Patent
Hutchinson

(10) Patent No.: US 9,211,087 B2
(45) Date of Patent: Dec. 15, 2015

(54) SELF-CONTAINED HAND-HELD TEST DEVICE FOR SINGLE-USE

(71) Applicant: Animas Corporation, West Chester, PA (US)

(72) Inventor: Michael Hutchinson, King of Prussia, PA (US)

(73) Assignee: Animas Corporation, West Chester, PA (US)

( * ) Notice: Subject to any disclaimer, the term of this patent is extended or adjusted under 35 U.S.C. 154(b) by 662 days.

(21) Appl. No.: 13/654,428

(22) Filed: Oct. 18, 2012

(65) Prior Publication Data

US 2014/0114155 A1    Apr. 24, 2014

(51) Int. Cl.
| | | |
|---|---|---|
| G01N 27/327 | (2006.01) | |
| A61B 5/15 | (2006.01) | |
| A61B 5/1477 | (2006.01) | |
| A61B 5/151 | (2006.01) | |
| A61B 5/157 | (2006.01) | |
| A61B 5/145 | (2006.01) | |

(52) U.S. Cl.
CPC .............. *A61B 5/1411* (2013.01); *A61B 5/1477* (2013.01); *A61B 5/157* (2013.01); *A61B 5/150022* (2013.01); *A61B 5/15105* (2013.01); *A61B 5/15142* (2013.01); *A61B 5/150183* (2013.01); *A61B 5/150358* (2013.01); *A61B 5/150549* (2013.01); *A61B 5/150717* (2013.01); *A61B 5/14532* (2013.01); *A61B 5/150412* (2013.01); *A61B 2562/0295* (2013.01)

(58) Field of Classification Search
None
See application file for complete search history.

(56) References Cited

U.S. PATENT DOCUMENTS

| | | | | |
|---|---|---|---|---|
| 4,627,445 | A | * | 12/1986 | Garcia et al. .................. 600/583 |
| 4,945,313 | A | | 7/1990 | Brilka et al. |
| 5,708,247 | A | | 1/1998 | McAleer et al. |
| 5,951,836 | A | | 9/1999 | McAleer et al. |
| 6,241,862 | B1 | | 6/2001 | McAleer et al. |
| 6,284,125 | B1 | | 9/2001 | Hodges et al. |
| 6,413,410 | B1 | | 7/2002 | Hodges et al. |
| 6,733,655 | B1 | | 5/2004 | Davies et al. |
| 7,112,265 | B1 | | 9/2006 | McAleer et al. |
| 7,214,542 | B2 | | 5/2007 | Hutchinson |
| 7,220,597 | B2 | | 5/2007 | Zin et al. |
| 7,241,265 | B2 | | 7/2007 | Cummings et al. |
| 7,250,105 | B1 | | 7/2007 | Davies et al. |

FOREIGN PATENT DOCUMENTS

EP          1 048 310        1/2007

* cited by examiner

*Primary Examiner* — J. Christopher Ball

(57) ABSTRACT

A self-contained hand-held test device for the single-use determination of an analyte (such as glucose) in a bodily fluid sample (for example, a whole blood sample) includes a housing with proximal and distal ends, a housing cap configured for removable attachment to the distal end of the housing, a single analytical test strip (e.g., a single electrochemical-based analytical test strip) disposed partially in the housing and extending from the distal end thereof, a meter module disposed in the housing, and a lancing module attached to the proximal end of the housing. The lancing module is configured to lance a user's target site (such as a fingertip or other suitable site) for the expression of a bodily fluid sample. In addition, the single analytical test strip has a bodily fluid sample application portion and a meter module contact portion and is operably connected to the meter module in user irreplaceable manner.

22 Claims, 9 Drawing Sheets

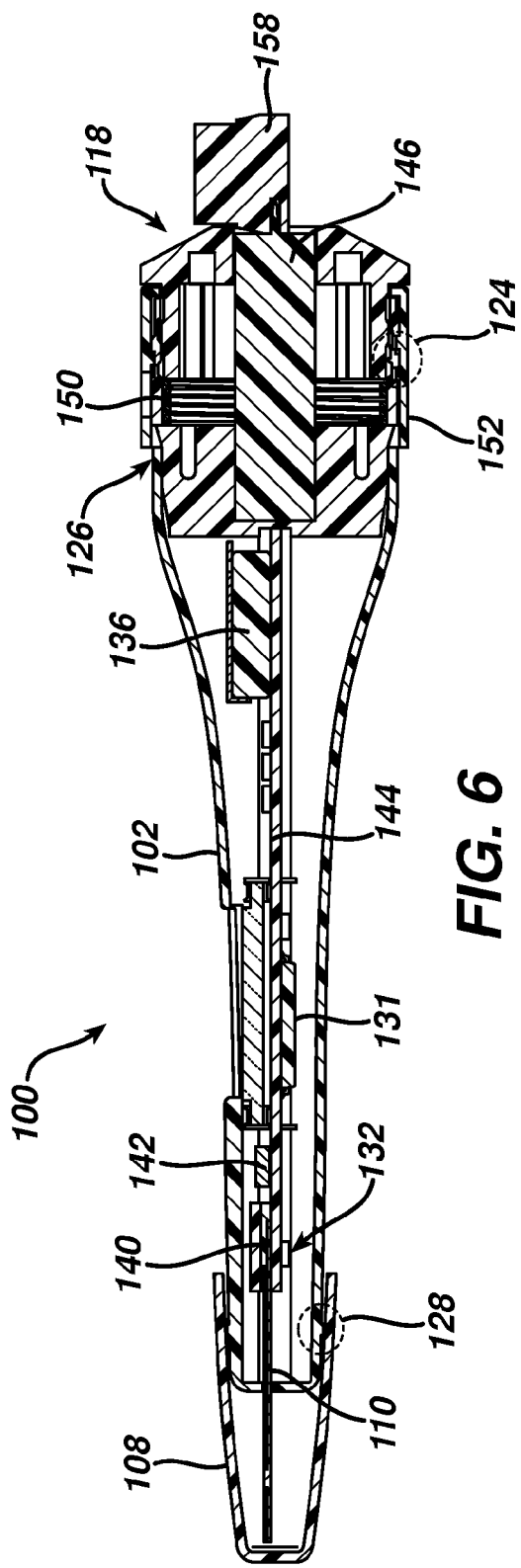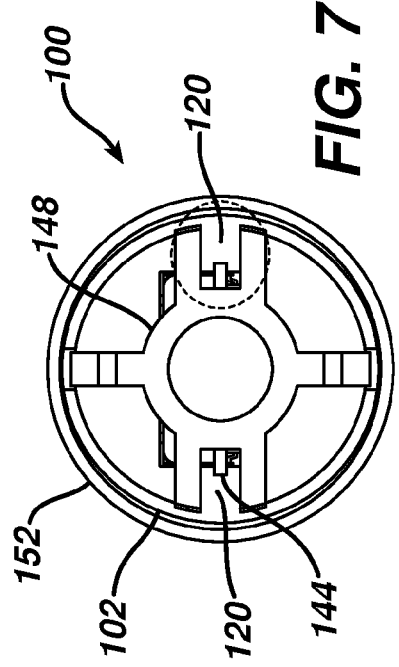

SELF-CONTAINED HAND-HELD TEST DEVICE FOR SINGLE-USE

BACKGROUND OF THE INVENTION

1. Field of the Invention

The present invention relates, in general, to medical devices and, in particular, to test devices and related methods.

2. Description of Related Art

The determination (e.g., detection and/or concentration measurement) of an analyte in a fluid sample is of particular interest in the medical field. For example, it can be desirable to determine glucose, ketone bodies, cholesterol, prostate-specific antigens (PSA), lipoproteins, triglycerides, acetaminophen and/or HbA1c concentrations in a sample of a bodily fluid such as blood, plasma or interstitial fluid. Such determinations are conventionally achieved by employing a multi-use hand-held test meter and a multi-use lancing device in combination with single-use analytical test strips (e.g., electrochemical-based analytical test strips).

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings, in which like numerals indicate like elements, of which:

FIG. 6 is a simplified cross-sectional side view of the self-contained hand-held test device of FIG. 1;

FIG. 7 is a simplified cross-sectional end view of the self-contained hand-held test device of FIG. 1;

DETAILED DESCRIPTION OF ILLUSTRATIVE EMBODIMENTS

Figure 1:
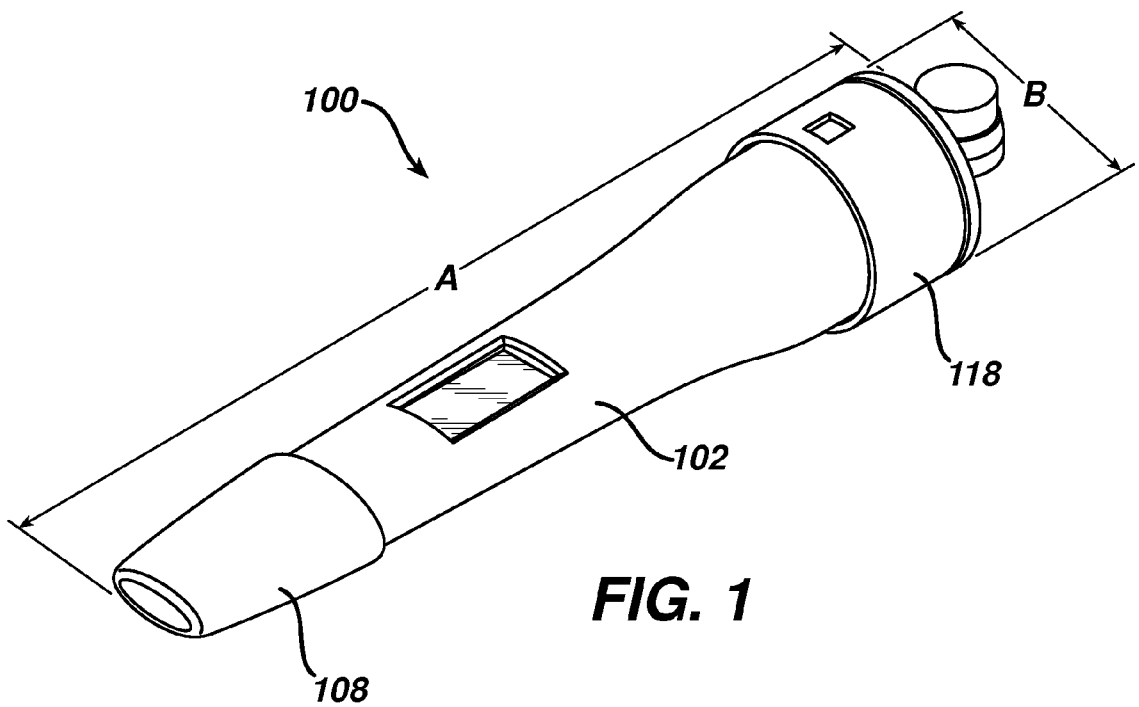
FIG. 1 is a simplified perspective depiction of a self-contained hand-held test device for the single-use determination of an analyte in a bodily fluid sample according to an embodiment of the present invention.

The following detailed description should be read with reference to the drawings, in which like elements in different drawings are identically numbered. The drawings, which are not necessarily to scale, depict exemplary embodiments for the purpose of explanation only and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein.

Self-contained hand-held test device for the single-use determination of an analyte (such as glucose) in a bodily fluid sample (for example, a whole blood sample) according to embodiments of the present invention include a housing with proximal and distal ends, a housing cap configured for removable attachment to the distal end of the housing, a single analytical test strip (e.g., a single electrochemical-based analytical test strip) disposed partially in the housing and extending from the distal end thereof, a meter module disposed at least partially in the housing, and a lancing module attached to the proximal end of the housing and configured to lance a user's target site (such as a fingertip or other suitable target site) for the expression of a bodily fluid sample. In addition, the single analytical test strip has a bodily fluid sample application portion and a meter module contact portion and is operably connected to the meter module in a user irreplaceable manner.

Self-contained hand-held test devices according to embodiments of the present invention are beneficial in that, for example, the self-contained hand-held test device is simple, convenient, and easy to use since a user is not required to carry separate lancets, lancing device, analytical test strips and meter but rather need carry only a self-contained hand-held test device according to embodiments of the present invention. Moreover, since self-contained hand-held test devices according to embodiments of the present invention are configured for a single use, they are discarded in a suitably safe manner following such use, thereby minimizing the risk of contamination and spread of disease during a subsequent use.

It is envisioned that the single use nature of self-contained hand-held test devices according to embodiments of the present invention will be particularly beneficial in a trauma situation where a quick single determination of a victim's blood glucose is needed, in hospital settings where the spread of disease is a concern, for use by newly diagnosed patients prior to their training in the use of more complicated separate devices and for other users who require only a relatively infrequent determination of an analyte in a bodily fluid sample.

Figure 2:
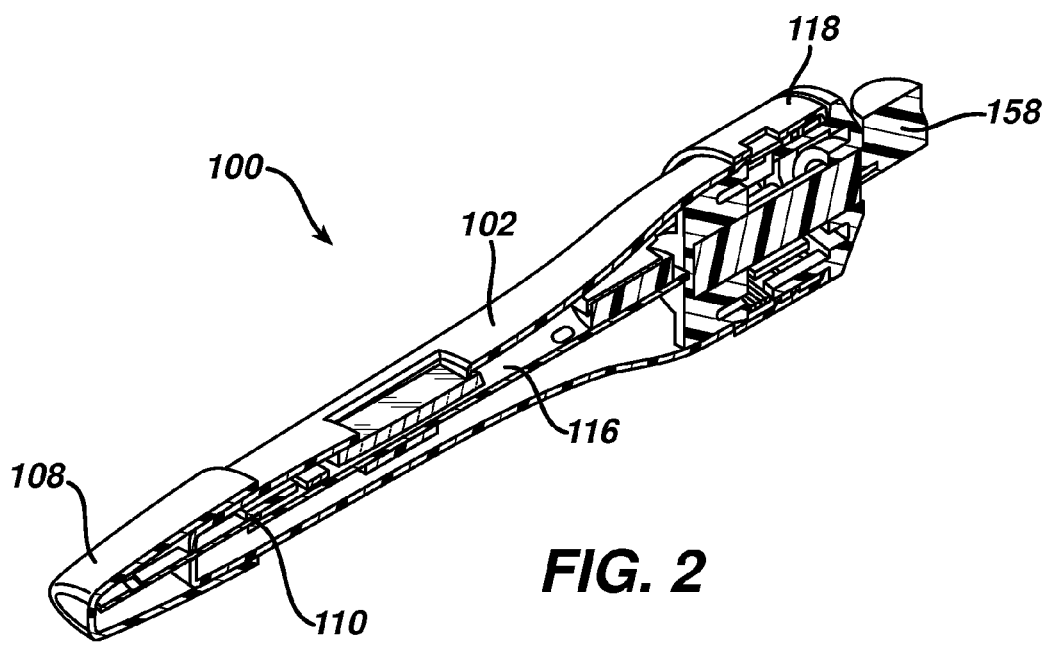
FIG. 2 is a simplified cross-sectional perspective view of the self-contained hand-held test device of FIG. 1.
Figure 3:
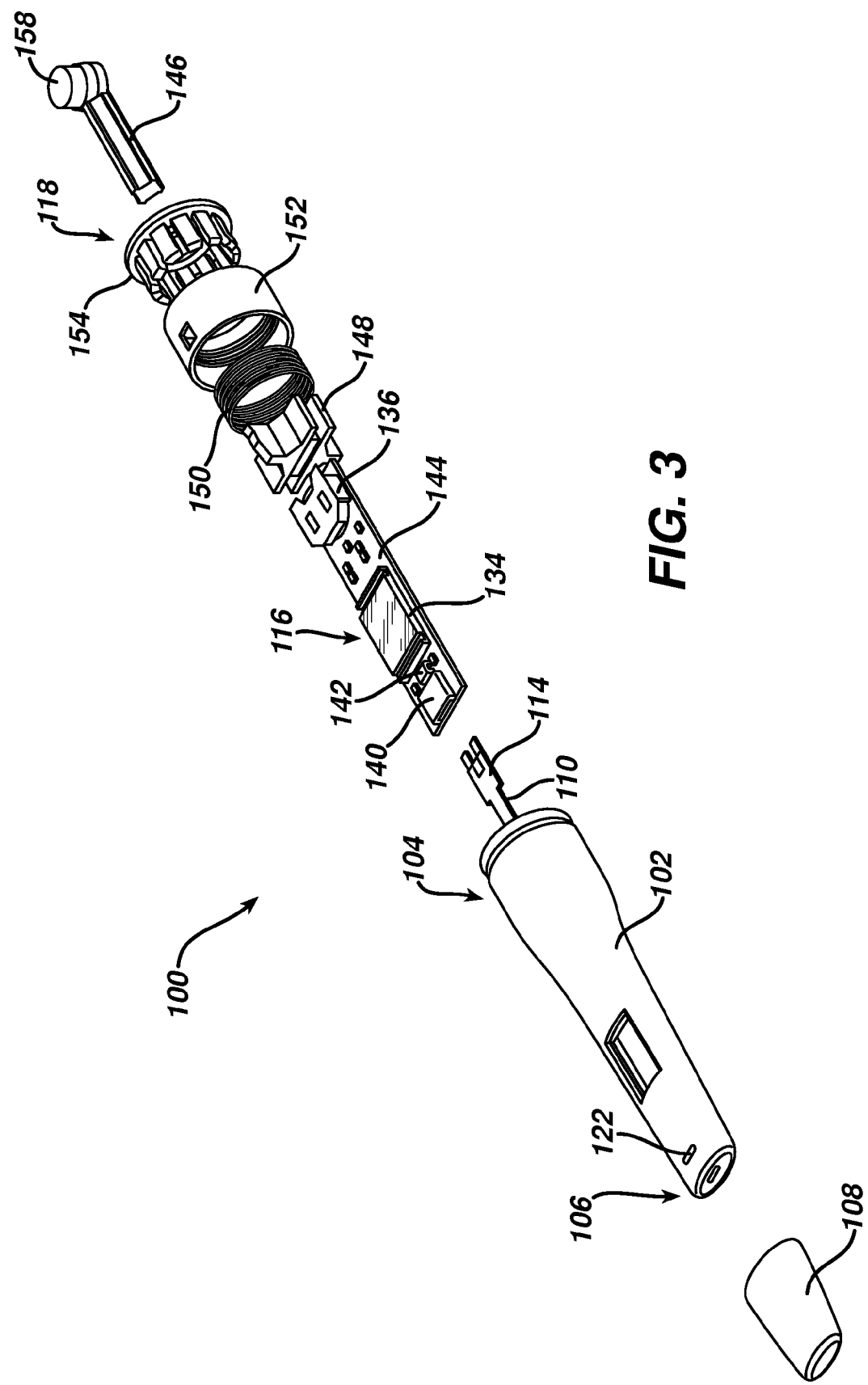
FIG. 3 is a simplified, exploded perspective depiction of the self-contained hand-held test device of FIG. 1.
Figure 4:
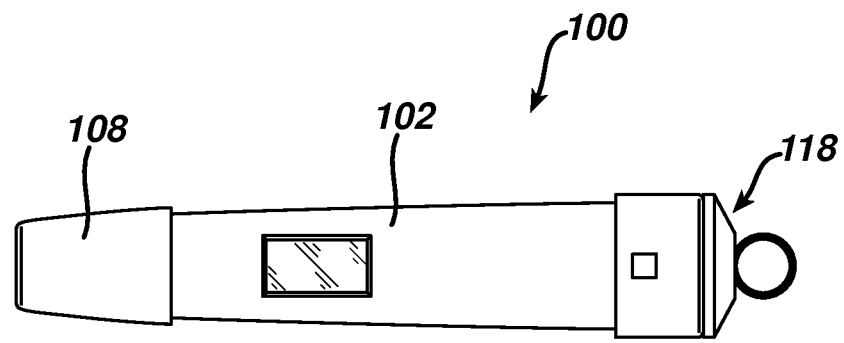
FIG. 4 a simplified top view of the self-contained hand-held test device of FIG. 1.
Figure 5:
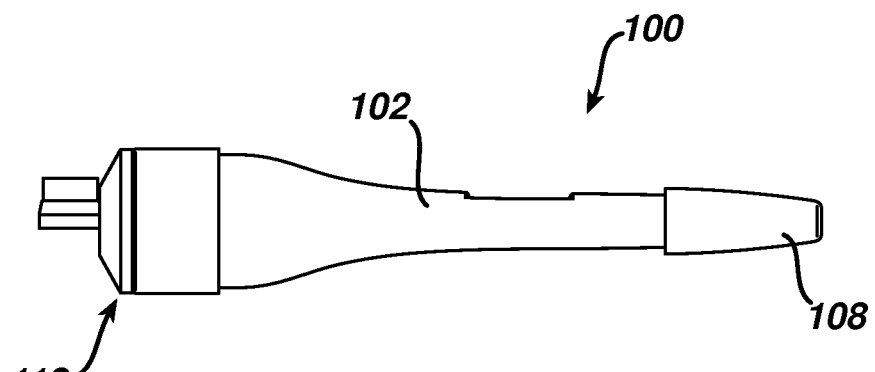
FIG. 5 is a simplified side view of the self-contained hand-held test device of FIG. 1.

FIG. 1 is a simplified perspective depiction of a self-contained hand-held test device 100 for the single-use determination of an analyte in a bodily fluid sample according to an embodiment of the present invention. FIG. 2 is a simplified cross-sectional perspective view of self-contained hand-held test device 100. FIG. 3 is a simplified, exploded perspective depiction of self-contained hand-held test device 100. FIG. 4 a simplified top view of self-contained hand-held test device of 100. FIG. 5 is a simplified side view of the self-contained hand-held test device 100. FIG. 6 is a simplified cross-sectional side view of the self-contained hand-held test device 100 and FIG. 7 is a simplified cross-sectional end view of the self-contained hand-held test device 100.

Figure 8:
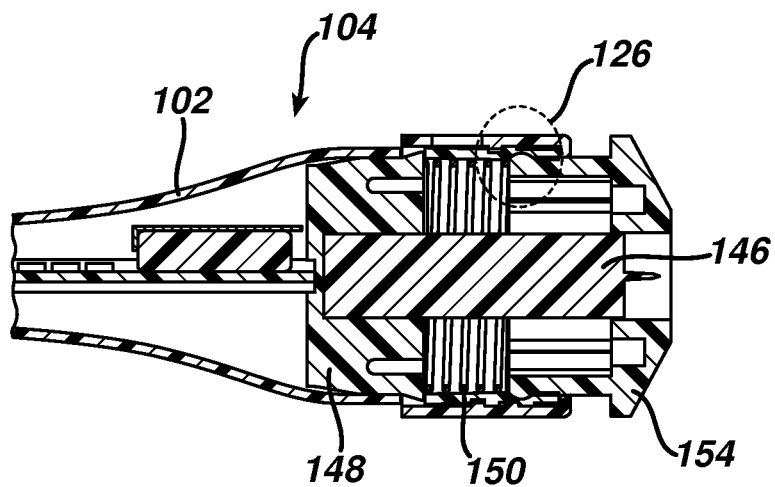
FIG. 8 is a simplified cross-sectional side view of the proximal end of the self-contained hand-held test device of FIG. 1 following removal of a lancet protective disk of the self-contained hand-held test device.
Figure 9:
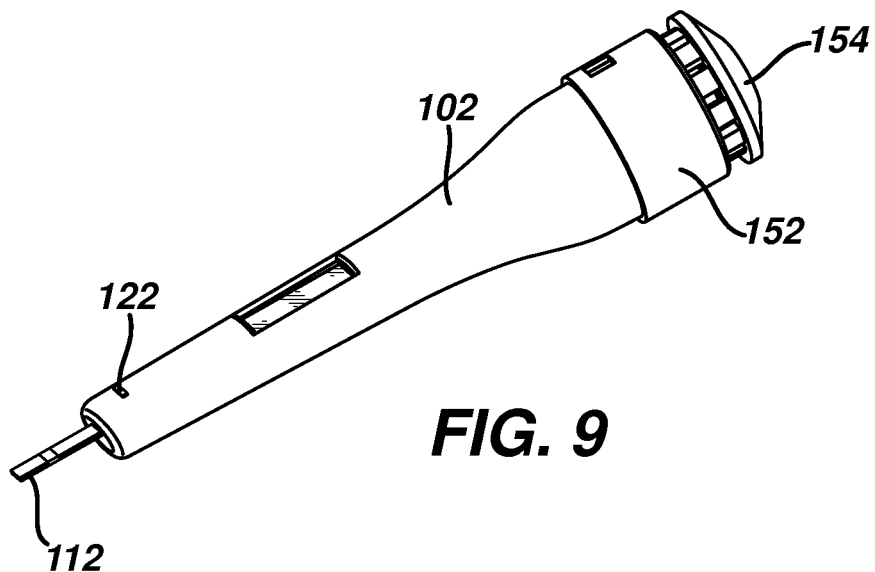
FIG. 9 is a simplified perspective view of the self-contained hand-held test device of FIG. 1 following removal of a housing cap and the lancet protective disk of the self-contained hand-held test device.
Figure 10:
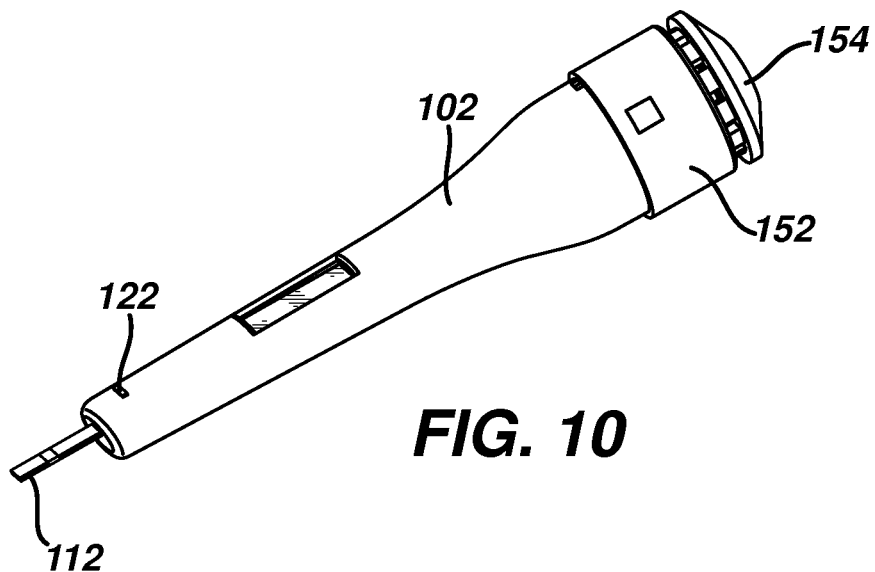
FIG. 10 simplified perspective view of the self-contained hand-held test device of FIG. 9 following rotation of the a height adjustment cap thereof.
Figure 11:
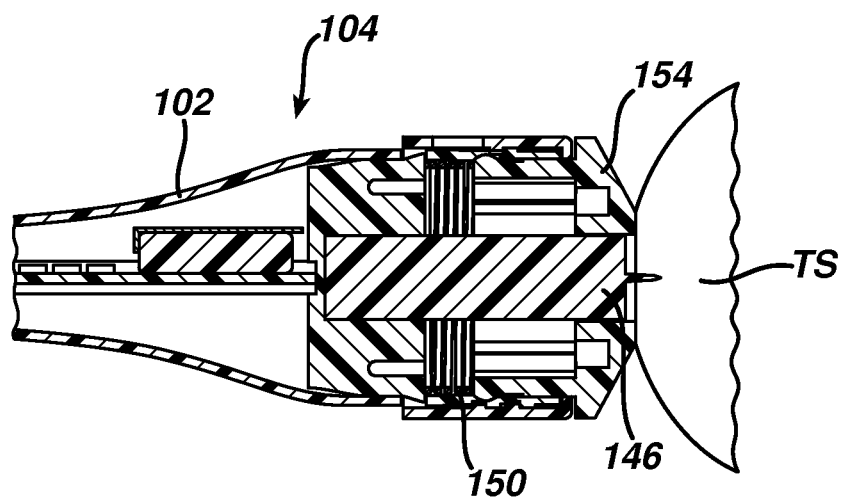
FIG. 11 is simplified cross-sectional side view of the proximal end of the self-contained hand-held test device of FIG. 1 compressed against a target site during lancing.
Figure 12:
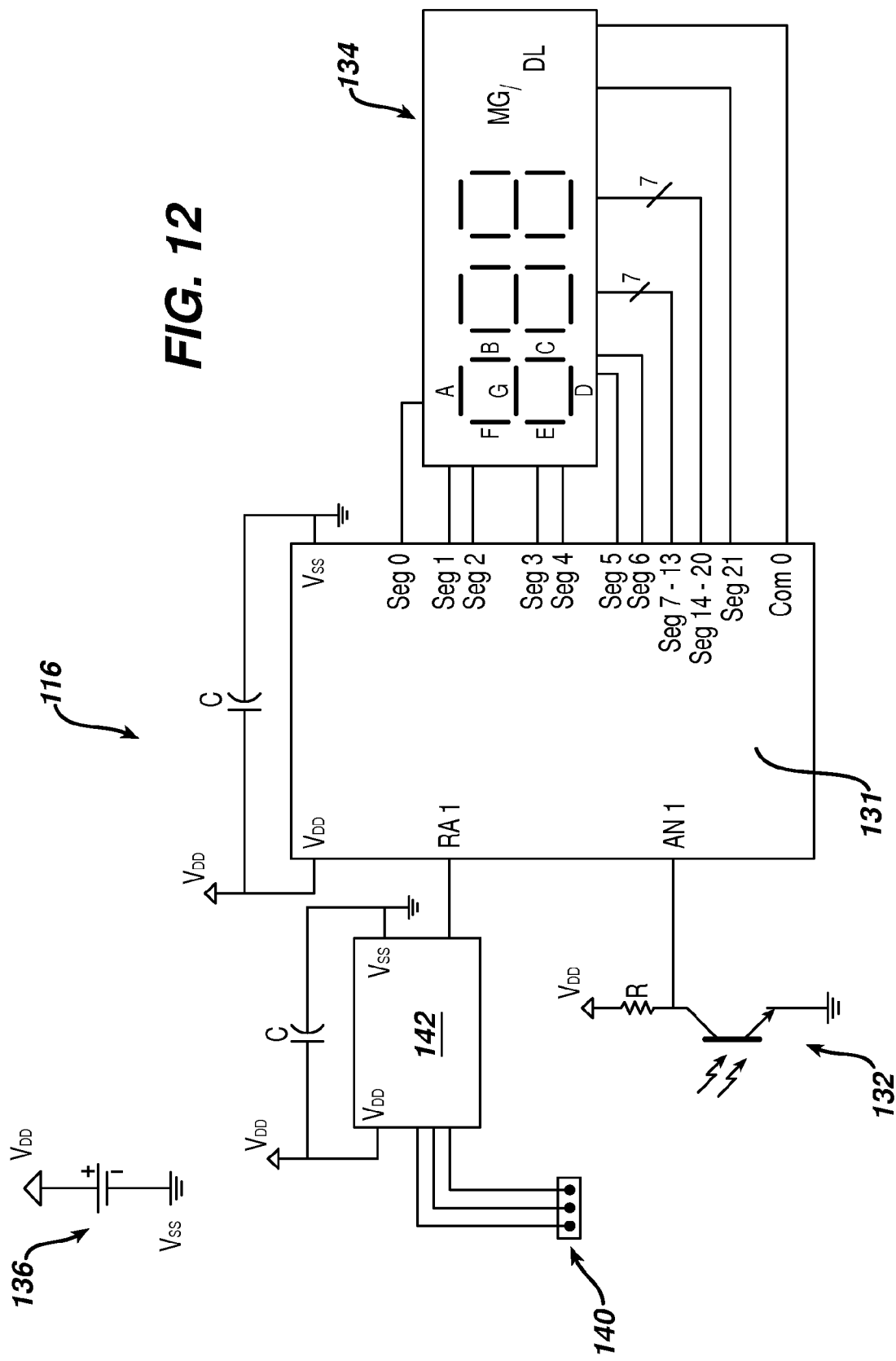
FIG. 12 is a simplified combined block and electrical schematic of various components of the self-contained hand-held test device of FIG. 1.

FIG. 8 is a simplified cross-sectional side view of the proximal end of self-contained hand-held test device 100 following removal of a lancet protective disk of the self-contained test device. FIG. 9 is a simplified perspective view of self-contained hand-held test device 100 following removal of a housing cap and the lancet protective disk of self-contained hand-held test device 100. FIG. 10 simplified perspective view of the self-contained hand-held test device as depicted in FIG. 9 following rotation of a height adjustment cap thereof. FIG. 11 is simplified cross-sectional side view of the proximal end of self-contained hand-held test device 100 compressed against a target site (TS) during lancing. FIG. 12 is a simplified combined block and electrical schematic of various components of self-contained hand-held test device 100.

Referring to FIGS. 1 through 11, self-contained hand-held test device 100 includes a housing 102 with a proximal end 104 and a distal end 106. Self-contained hand-held test device 100 also includes a housing cap 108 configured for removable attachment to distal end 106 and a single analytical test strip 110 disposed partially in housing 102 and extending from distal end 106. Single analytical test strip 110 has a bodily fluid sample application portion 112 (see, in particular, FIGS. 9 and 10) and a meter contact portion 114.

Self-contained hand-held test device 100 also includes a meter module 116 disposed in housing 102 and a lancing module 118 attached to proximal end 104 of housing 102. Lancing module 118 is configured to lance a user's target site (such as a fingertip) for the expression of a bodily fluid sample therefrom.

In the embodiment of FIGS. 1 through 7, single analytical test strip 110 is operably connected to meter module 116 in a user irreplaceable manner via at least meter contact portion 114.

The dimensions of self-contained hand-held test meter 100 are predetermined such that self-contained hand-held test meter 100 can be easily held in a single hand by a user. For example, in FIG. 1 dimension "A" can be 4 inches and dimension "B" can be 0.875 inches.

Housing 102 can be made of any suitable material including, for example, injection molded plastic. Internal surfaces of housing 102 include alignment rails 120 (see FIG. 7 wherein one of the alignment rails is circled by a dashed line) configured to securely hold meter module 116 and lancing module 118. Distal end 106 of housing 102 is configured to prevent the removal and replacement of single analytical test strip 110 by a user. Distal end 106 can prevent removal and replacement of single analytical test strip 110 by, for example, being configured to allow single analytical test strip 110 to extend therefrom (see FIGS. 6, 9 and 10 in particular), but to not allow the entire length of the single analytical test strip (which typically varies in width along its length) to be pulled therefrom.

Housing 102 also includes an ambient light opening 122 (see FIGS. 3, 9 and 10 in particular) configured to allow ambient light to enter housing 102 when housing cap 108 is removed. Housing 102 further includes threads 124 (shown within a dashed circle in FIG. 6) and recesses 126 (see FIG. 6 and the dashed circle of FIG. 8 in particular) on an external surface of proximal end 104, for securing lancing module 118. In addition, housing 102 includes protrusions 128 (also shown within a dashed circle of FIG. 6) on an external surface of distal end 106 configured to provide a removable fit for housing cap 108.

Housing cap 108 can be formed of any suitable material including, for example, injection molded plastic. Housing cap 108 includes recessed areas 130 on an inner surface configured to mate with protrusions 128 of housing 102 (see FIG. 6 in particular). Housing cap 108 is also configured to block ambient light opening 122 when attached to housing 102 thus preventing light from entering housing 102.

Meter module 116 includes a microcontroller 131, an ambient light sensor 132 (e.g., a phototransistor), an LCD display 134, a battery 136 (such as a non-rechargeable battery), a strip port connector 140 a blood-glucose (BG) sub-module 142, and a printed circuit board 144. Microcontroller 131 can be any suitable microcontroller including, for example, a microcontroller with integrated LCD driver available from Microchip as part number PIOC18F85J90. Such a microcontroller is configured to control meter module 116.

Meter module 116 is essentially constructed as a printed circuit board assembly with printed circuit board (PCB) 144 being a four-layer two-sided PCB.

LCD display 134 can be any suitable LCD display including, for example, a 22 segment single backplane display configured to display three characters and one symbol. The symbol can be, for example, mL/dL or mmol/L. Battery 136 can be any suitable battery including, for example, a 3V coin cell battery. Battery 136 can be permanently sealed within housing 102 and be configured to store power that is only sufficient to enable a single determination by self-contained hand-held test device 100 under typical use conditions. For example, battery 136 can be configured to store approximately 20 mAh to 30 mAh of power and provide for 6 months of shelf-life and less than 24 hours of use following activation of the self-contained hand-held test device.

Ambient light sensor 132 is configured, along with ambient light opening 122 and the remainder of meter module 116 to activate the self-contained hand-held test meter when ambient light entering through ambient light opening 122 strikes ambient light sensor 132. Such light enters through ambient light opening 122 when housing cap 108 is removed from housing 102 during use of self-contained hand-held test device 100. Alternatively, light can be blocked from entering ambient light opening 122 by an opaque outer package. Once such an opaque outer package is removed by a user, ambient light enters housing 102, strikes ambient light sensor 132, thus activating the self-contained hand-held test meter.

Strip port connector 140 is configured to operatively interface with the single analytical test strip 110 via meter contact portion 114. Blood glucose sub-module 142 is configured to receive an electrochemical response signal from the single analytical test strip (via strip port connector 140) and convert that electrochemical response signal into a converted signal that is transmitted to microcontroller 131 for processing (see, for example, FIG. 12). Microcontroller 131 processes the converted signal into, for example, a blood glucose concentration that is displayed in LCD display 134.

Meter module 116 of self-contained hand-held test device 100 also includes and other electronic components (not shown) for applying a test voltage to single analytical test strip 110, and also for measuring an electrochemical response (e.g., a plurality of test current values) and determining an analyte based on the electrochemical response. To simplify the current descriptions, the figures do not depict all such electronic circuitry.

Lancing module 118 includes a lancet 146, a lancet retainer 148, a lancet spring 150, a lancet height adjustment cap 152, a lancet guard 154 and a lancet protective disk 158. Lancet 146 can be any suitable lancet known to one skilled in the art.

Lancet retainer 148 is configured to securely hold (i.e., retain) lancet 146 and can be formed of any suitable material including injection molded plastic. Lancet retainer 148 is assembled, and held within, in housing 102 via alignment rails 120.

Lancet spring 150 can be any suitable spring including a compression spring with ground ends. Lancet spring 150 is configured to apply a force on lancet guard 154 following removal of lancet protective disk 158. Such force positions lancet guard 154 such that lancet 146 is shielded (see FIG. 8 in particular).

Lancet height adjustment cap 152 is configured for a user to set the lancing depth of lancet 146 via rotation of the lancet height adjustment cap and can be formed from, for example, a suitable plastic material.

Lancet guard 154 is initially forced inward into housing 102 during assembly of self-contained hand-held test device 100, thus compressing lancet spring 150 (see FIG. 6 in particular). Upon removal of lancet protective disk 158, lancet guard 154 is partially slid out of housing 102 by the force applied by lancet spring 150 (see FIG. 8 such that lancet guard 154 shields lancet 150 (see FIG. 8 in particular). Lancet guard 154 is configured to prevent a user from removing lancet 146 from lancing module 118 by, for example, blocking access that would enable a user to grasp lancet 146 and pull it from lancing module 118. Such blocked access prevents a user from removing lancet 146, replacing it with another lancet, and reusing self-contained hand-held test device 100 for lancing a target site.

Lancet protective disk 158 can be formed from any suitable material including, for example, plastic materials. Lancet protective disk 158 is configured to encase lancet 146 during shipment and prior to use of self-contained hand-held test device 100. However, lancet protective disk 158 is also configured for easy removal by a user.

To employ self-contained hand-held test device 100, a user removes any outer package such as, for example, a foil wrap hermetically sealed package known to those of skill in the art (not depicted in the FIGs.). Self-contained hand-held test device 100 would then appear as depicted in, for example, FIG. 1. Subsequently, the user would remove housing cap 108, thus allowing ambient light to enter housing 102 via ambient light opening 122 and strike ambient light sensor 132 of meter module 116. In response to light striking ambient light sensor 132, self-contained hand-held test device 100 is activated into an operational mode. Such an operational mode can be, if desired, indicated to a user by flashing of LCD display 134 or other suitable means.

The user then removes lancet protective disk 158 from lancet module 118. Such removal enables lancing module 118 and pushes lancet guard 154 away from proximal end 104 of housing 102 due to the force of lancet spring 150 (as is evident from a comparison of FIGS. 6 and 8). Self-contained hand-held test device 100 then appears as in FIG. 9.

The user would then select a desired lancing depth by rotating lancet height adjustment cap 152 to obtain a desired depth setting (see FIGS. 9 and 10 in particular). The user then lances a target site (such as a fingertip target site) by pressing self-contained hand-held device 100 against the target site as depicted in FIG. 11. The pressing occurs against the force of lancet spring 150 and results in lancet guard 154 being moved toward housing 102 and lancet 146 penetrating the target site (see FIG. 11). As the user presses, the applied force results removes lancet guard 156 from recesses 126, thus providing a snap-like action during lancing. After lancet 146 penetrates the target site, the user immediately removes self-contained hand-held test device from the target site and lancet guard 154 moves under the force of lancet spring 150 to once again shield lancet 146.

A bodily fluid sample expressed from the lanced target site is then applied to bodily fluid sample application portion 112 of single analytical test strip 110. Bodily fluid sample application portion 112 is exposed for application of the bodily fluid sample since the removal of housing cap 108 exposes bodily fluid sample application portion 112 (see, for example, FIG. 9). Self-contained hand-held test meter 100 then automatically determines an analyte in the applied bodily fluid sample (using the electronics of meter module 116) and displays the results on LCD display 134.

Since self-contained hand-held test device 100 is configured for single use and not capable of performing any additional determinations, the self-contained hand-held test device (included the removed housing cap and lancet protective disk) is then discarded. If desired, a user can reposition the housing cap back on the housing via a snap-fit prior to discarding the self-contained hand-held test device.

Once one skilled in the art is apprised of the present disclosure, he or she will recognize that various commercially available meter modules (or components thereof), lancing modules, lancets, and single analytical test strips can be employed in and/or modified for employment in self-contained hand-hand test devices according to embodiments of the present invention.

Moreover, the single analytical test strip can be any suitable analytical test strip including an electrochemical-based analytical test strip such as the commercially available One-Touch® Ultra® glucose test strip from LifeScan Inc. (Milpitas, Calif.). Examples of analytical test strips can be found in U.S. Pat. Nos. 5,708,247; 5,951,836; 6,241,862; 6,284,125; 6,413,410; 6,733,655; 7,112,265; 7,241,265; and 7,250,105, each of which is hereby incorporate herein in full by reference.

If desired, self-contained hand-held test device 100 or other embodiments of self-contained hand-held test devices according to embodiments of the present invention can be modified to provide for Radio-Frequency (RF) or other wireless communication of determination results to a compatible device (e.g., an insulin pump, personal computer or phone) by the inclusion of a suitable RF communication module. In addition, a suitable Universal Serial Bus (USB) interface can be added to provide for data download capability. In either of these options, the LCD display depicted in the FIGs. could, if desired, be eliminated.

Figure 13:
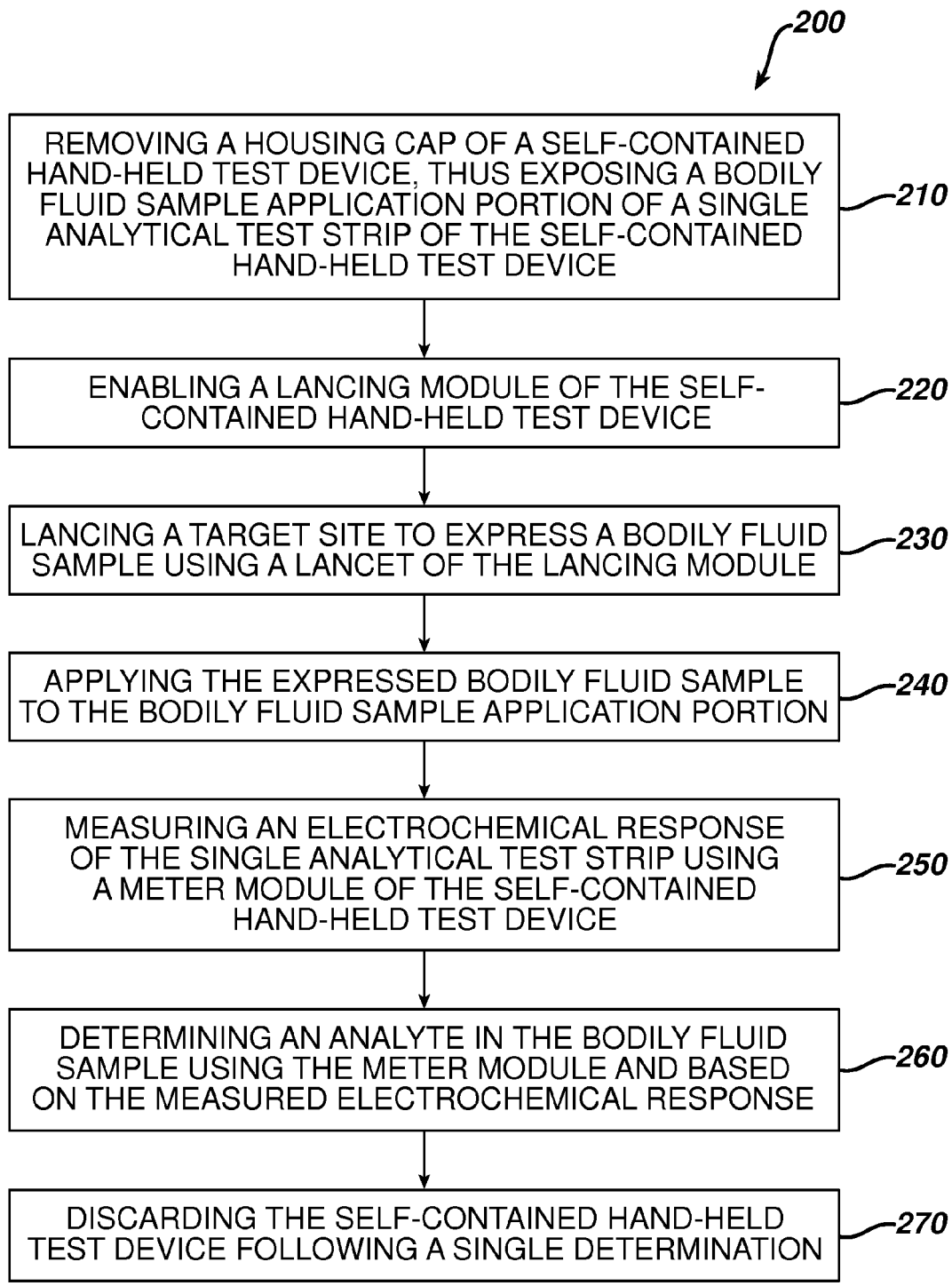
FIG. 13 is a flow diagram depicting stages in a method for the determination of an analyte in a bodily fluid sample according to an embodiment of the present invention.

FIG. 13 is a flow diagram depicting stages in a method 200 for the determination of an analyte (such as glucose) in a bodily fluid sample (e.g., a whole blood sample). Method 200 includes removing a housing cap of a self-contained hand-held test device from a distal end of the self-contained hand-held test device, thus exposing a bodily fluid sample application portion of a single analytical test strip of the self-contained hand-held test device. See step 210 of FIG. 13.

The method further includes enabling a lancing module of the self-contained hand-held test device (see step 220 of FIG. 13) and lancing a target site to express a bodily fluid sample therefrom using a lancet of the lancing module (see step 230 of FIG. 13).

Method 200 also includes, at step 240, applying the expressed bodily fluid sample to the bodily fluid sample application portion of the single analytical test strip. Subsequently, at step 250, an electrochemical response of the single analytical test strip is measured using a meter module of the self-contained hand-held test device and, at step 260, the analyte is determined using the meter module based on the measured electrochemical response.

Referring to step 270 of FIG. 13, following a single determination, the self-contained hand-held test device is discarded. It is noted that in method 200, the single analytical test strip is operably connected to the meter module in a user irreplaceable manner via at least the meter contact portion of the single analytical test strip.

Once apprised of the present disclosure, one skilled in the art will recognize that method 200 can be readily modified to incorporate any of the techniques, benefits and characteristics of self-contained hand-held test devices according to embodiments of the present invention and described herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that devices and methods within the scope of these claims and their equivalents be covered thereby.

What is claimed is:

1. A self-contained hand-held test device for the single-use determination of an analyte in a bodily fluid sample, the self-contained test device comprising:
    a housing with:
        a proximal end;
        a distal end; and
        a housing cap configured for removable attachment to the distal end of the housing;
    a single analytical test strip disposed partially in the housing and extending from the distal end thereof, the single analytical test strip having:
        a bodily fluid sample application portion; and
        a meter module contact portion;
    a meter module disposed in the housing; and
    a lancing module attached to the proximal end of the housing and configured to lance a user's target site for the expression of a bodily fluid sample, and
    wherein the single analytical test strip is operably connected to the meter module in a user irreplaceable manner.

2. The self-contained hand-held test device of claim 1 wherein from the housing, housing cap and meter module are configured such that removal of the housing cap from the housing results in automatic activation of the self-contained hand-held test device and exposes the bodily fluid sample application portion of the single analytical test strip.

3. The self-contained hand-held test device of claim 1 further comprising an outer package enclosing the housing, housing cap, single analytical test strip, meter module, and lancing module.

4. The self-contained hand-held test device of claim 1 wherein the lancing module includes:
    a lancet;
    a lancet retainer;
    a lancet spring;
    a height adjustment cap; and
    a lancet guard,
    and wherein the lancet is user moveable, against a force generated by the lancet spring, between a staged position within the lancet guard and a lancing position extending from the lancet guard, and
    wherein the lancet guard is configured for placement against a target site.

5. The self-contained hand-held test device of claim 4 wherein the lancing module further includes a lancet protective disk, and
    wherein the lancet spring is configured to position the lancet guard, upon removal of the lancet protective disk, such that the lancet guard shields the lancet.

6. The self-contained hand-held test device of claim 1 wherein the housing further includes an ambient light opening and the meter module further includes an ambient light sensor, and
    wherein the ambient light opening and the ambient light sensor are configured to activate the self-contained hand-held test meter when the housing cap is removed and ambient light enter the housing through the ambient light opening.

7. The self-contained hand-held test device of claim 1 wherein the meter module includes a non-rechargeable battery permanently sealed within the housing.

8. The self-contained hand-held device of claim 6 wherein the non-rechargeable battery stores an electrical charge sufficient to power the self-contained hand-held device following activation for less than 24 hours.

9. The self-contained test hand-held device of claim 1 wherein the meter module is configured for the determination of glucose in a whole blood sample.

10. The self-contained hand-held test device of claim 1 wherein the distal end of the housing is configured to prevent removal and replacement of the single analytical test strip by a user.

11. The self-contained hand-held test device of claim 1 further including a Universal Serial Bus (USB) interface.

12. The self-contained hand-held test device of claim 1 further including a Radio Frequency (RF) communication module.

13. A method for the determination of an analyte in a bodily fluid sample, the method comprising:
    removing a housing cap of a self-contained hand-held test device from a distal end of the self-contained hand-held test device, thus exposing a bodily fluid sample application portion of a single analytical test strip of the self-contained hand-held test device;
    enabling a lancet module of the self-contained hand-held test device;
    lancing a target site to express a bodily fluid sample therefrom using a lancet of the lancing module;
    applying the expressed bodily fluid sample to the bodily fluid sample application portion of the single analytical test strip;
    measuring an electrochemical response of the single analytical test strip using a meter module of the self-contained hand-held test device;
    determining, using the meter module, the analyte based on the measured electrochemical response; and
    discarding the hand-held self-contained test device after a single determining step,
    wherein the single analytical test strip is operably connected to the meter module in a user irreplaceable manner.

14. The method of claim 13 wherein the removing step also activates the meter module of the self-contained hand-held test device.

15. The method of claim 14 wherein the activating of the meter module occurs due to ambient light striking a light sensor of the meter module upon removal of the housing cap.

16. The method of claim 13 wherein the bodily fluid sample is a whole blood sample.

17. The method of claim 16 wherein the analyte is glucose.

18. The method of claim 13 wherein the single analytical test strip is an electrochemical-based analytical test strip.

19. The method of claim 13 wherein the enabling step involves removing a lancet protective disk from the lancet module.

20. The method of claim 13 further including adjusting a lancing depth by rotating a height adjustment cap of the lancing module prior to lancing the target site.

21. The method of claim 13 wherein the lancing of the target site occurs against a force generated by a lancet spring of the lancing module.

22. The method of claim 13 further including removing an outer package of the self-contained hand-held test device prior to the removing of the housing cap.

\* \* \* \* \*